(12) United States Patent
McDaniel et al.

(10) Patent No.: US 7,602,486 B2
(45) Date of Patent: Oct. 13, 2009

(54) COOLANT PASSAGE INSPECTION DEVICE AND METHOD OF VEHICLE CYLINDER HEAD COOLANT PASSAGE BLOCKAGE DETECTION

(75) Inventors: Marc McDaniel, Botkins, OH (US); Charles Hoke, Piqua, OH (US); Chad J. Miller, Minster, OH (US); Stephen A. Schumann, Troy, OH (US)

(73) Assignee: Honda Motor Co., Ltd., Tokyo (JP)

( * ) Notice: Subject to any disclaimer, the term of this patent is extended or adjusted under 35 U.S.C. 154(b) by 398 days.

(21) Appl. No.: 11/694,045

(22) Filed: Mar. 30, 2007

(65) Prior Publication Data

US 2008/0239303 A1  Oct. 2, 2008

(51) Int. Cl.
*G01N 21/00* (2006.01)
(52) U.S. Cl. .................................. 356/241.1; 356/237.6
(58) Field of Classification Search ........................ None
See application file for complete search history.

(56) References Cited

U.S. PATENT DOCUMENTS

| | | |
|---|---|---|
| 3,244,894 A | 4/1966 | Steele et al. |
| 4,383,761 A | 5/1983 | Jones |
| 4,409,718 A | 10/1983 | Pryor |
| 4,469,164 A | 9/1984 | Ishikawa et al. |
| 4,515,479 A | 5/1985 | Pryor |
| 4,654,949 A | 4/1987 | Pryor |
| 4,774,751 A | 10/1988 | Pryor |
| 5,506,682 A | 4/1996 | Pryor |
| 5,822,057 A | 10/1998 | Samman |
| 5,974,643 A | 11/1999 | Hays et al. |
| 6,259,523 B1 | 7/2001 | Welker |

FOREIGN PATENT DOCUMENTS

JP    2001317917 A  * 11/2001

* cited by examiner

*Primary Examiner*—L. G. Lauchman
*Assistant Examiner*—Amanda H Merlino
(74) *Attorney, Agent, or Firm*—Standley Law Group LLP

(57) ABSTRACT

A vehicle cylinder head coolant passage inspection device and a method for inspecting vehicle cylinder head coolant passages therewith. A device and method of the present invention can be used to detect blockages present within such coolant passages. A device and method of the present invention uses one or more fiber-optic probes that can both emit and receive light. The probe(s) are used with a sensor that can register light reflected by a blockage and received by a probe(s) while in a coolant passage. Reflected light readings registered by the sensor can be used to determine whether a blockage is present.

42 Claims, 14 Drawing Sheets

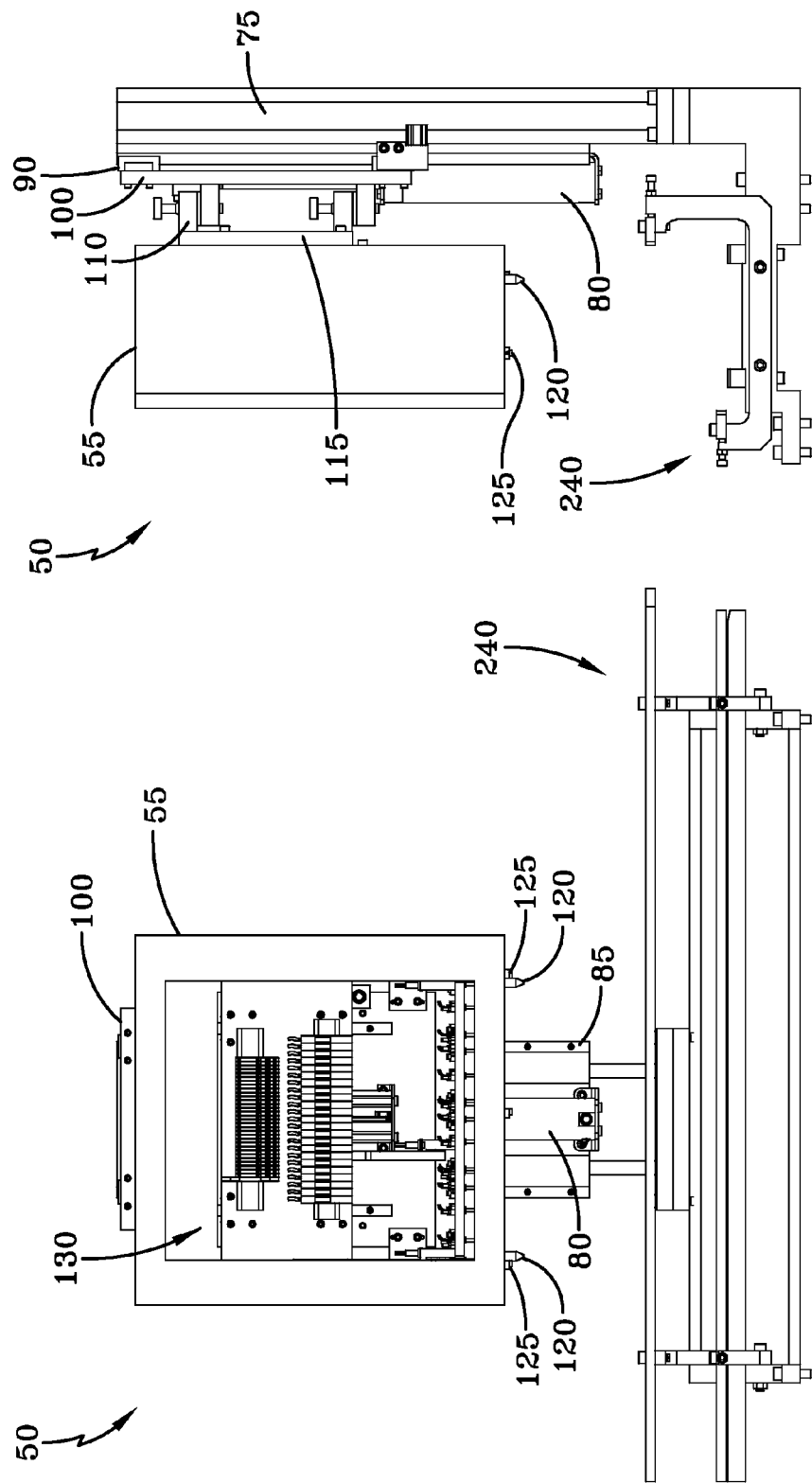

COOLANT PASSAGE INSPECTION DEVICE AND METHOD OF VEHICLE CYLINDER HEAD COOLANT PASSAGE BLOCKAGE DETECTION

BACKGROUND OF THE INVENTIVE FIELD

The present invention is directed to a device and method for inspecting the internal coolant passages of vehicle cylinder heads for blockages. More particularly, the present invention is directed to a device and method for non-visually inspecting the internal coolant passages of vehicle cylinder heads for blockages.

It is well known that vehicle cylinder heads typically rely on a flow of coolant to prevent overheating. This coolant is typically supplied by a vehicle's cooling system, which generally includes a radiator and water pump. The coolant travels, among other paths, through a series of coolant passages that are internal to the cylinder heads.

The internal coolant passages within a cylinder head can be quite circuitous in nature, often having a plurality of pathways for carrying the coolant around the valve area, etc., of the cylinder head. The more complex the design of the cylinder head, the more circuitous the coolant passages are likely to be.

As cylinder head design becomes more complex, so too must the molds used to produce the cylinder heads. Particularly, the sand molds that are used to form the coolant passages of the finished cylinder heads have become more complex. Defects in these sand molds can lead to defects in the coolant passages of an associated cylinder head. For example, cracks or other defects in a sand mold can become filled with molten aluminum during the molding process, leading to blockages in the coolant passage(s) of the finished cylinder head.

Even partial blockage of a cylinder head coolant passage can lead to problems with an engine and/or a vehicle with which the cylinder head is eventually associated. For example, because a blockage(s) in a coolant passage(s) can inhibit or prevent the flow of coolant therethrough, engine overheating, valve or piston damage, and/or HVAC problems can result. As such, it is obvious that the detection of cylinder head coolant passage blockages is desirable in order to prevent such problems.

Because of the structural nature of a cylinder head, observation of the interior of its internal coolant passages is inherently difficult. Furthermore, even when a portion of a coolant passage can be visually observed, the size and/or overall tortuous shape thereof generally limits observation of the remainder of the passage. Consequently, visual examination of a coolant passage for blockages is generally limited to only a small fraction of its overall length.

To this end, a non-visual method of inspecting cylinder head coolant passages for blockages and a device for performing such an inspection are needed. The device and method of the present invention satisfies this need.

SUMMARY OF THE GENERAL INVENTIVE CONCEPT

A device and method of the present invention provides for the non-visual inspection of cylinder head coolant passages. More particularly, a device and method of the present invention employs one or more fiber optic probes to examine the coolant passages of a vehicle cylinder head and to indicate the presence of any blockages residing therein.

The number of fiber-optic probes used preferably coincides with the number of coolant passage entryways present in the cylinder head. Alternatively, and less efficiently, a lesser number of fiber-optic probes can be utilized and simply moved from coolant passage to coolant passage as needed to complete the inspection.

The fiber-optic probes are preferably attached to a central mounting plate, such that all the probes can be moved at the same time. The mounting plate and probes may form one component of a device of the present invention and can be associated with a motive assembly that employs a motive device, such as an electro-mechanical, pneumatic or hydraulic cylinder, that operates to insert and retract the fiber-optic probes to/from the coolant passages to be inspected. Alternatively, the mounting plate and probes may be associated with a robot that operates to insert and retract the fiber-optic probes to/from the coolant passages to be inspected.

The fiber-optic probes are preferably of a diffuse variety. That is, once inserted into the coolant passages, the fiber-optic probes emit light and, if a blockage is present, receive back a sufficient amount of reflected light to trigger an associated photoelectric switch or other light detecting element.

A device of the present invention may also include or be associated with one or more of a monitoring portion that employs a processor, software, an associated user interface and a display. The monitoring portion may allow a user of the device to receive alerts as to the presence of coolant passage blockages. The monitoring portion may also present a user with a visual representation of the blockage(s) location. By setting various threshold values, the monitoring portion may be able to determine whether the cylinder head can still be used despite the presence of a blockage (e.g., when the blockage is sufficiently small).

A device and method of the present invention can be used offline, or can be used on an assembly line at a location associated with manufacturing, assembly or inspection of cylinder heads. Regardless of how it is used, it can be understood from the foregoing description that a device and method of the present invention can be used to quickly and accurately determine whether any of the coolant passages of a vehicle cylinder head contain blockages. As such, a device and method of the present invention can be successfully used to minimize or eliminate the occurrence of defective cylinder heads being installed to engines and vehicles.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIGS. 4a-4c illustrate one exemplary embodiment of a coolant passage inspection device of the present invention, wherein the device includes a number of fiber-optic probes that are shown in a retracted position;

DETAILED DESCRIPTION OF EXEMPLARY EMBODIMENT(S)

Figure 1:
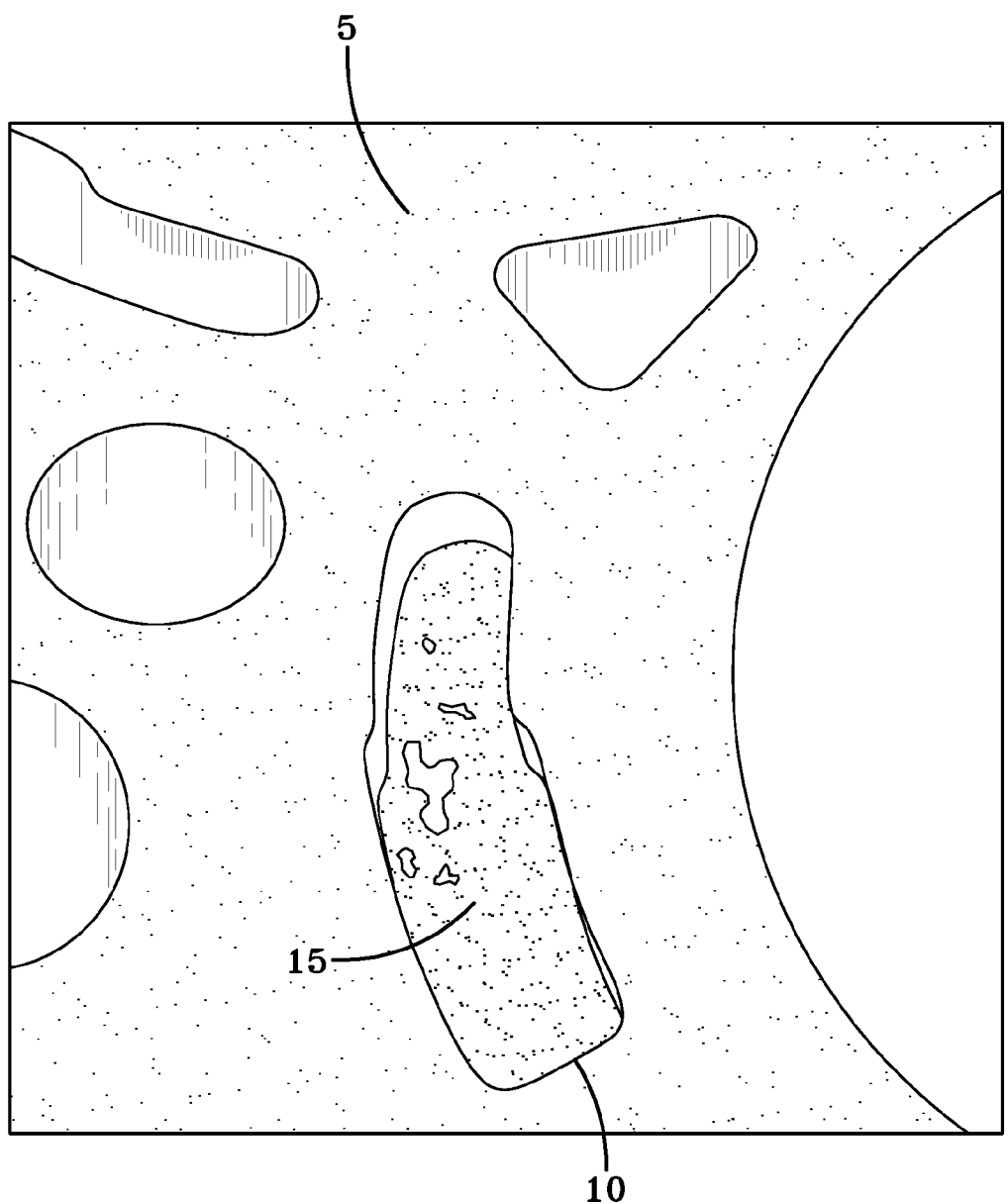
FIG. 1 shows a substantial blockage of a vehicle cylinder head coolant passage entryway.

As shown in FIGS. 1-2, vehicle cylinder head coolant passages can be blocked at various locations and to varying degree. For example, as shown in FIG. 1, an almost complete blockage 15 of a coolant passage 10 has occurred substantially at its entryway into the cylinder head 5.

Figure 2A:
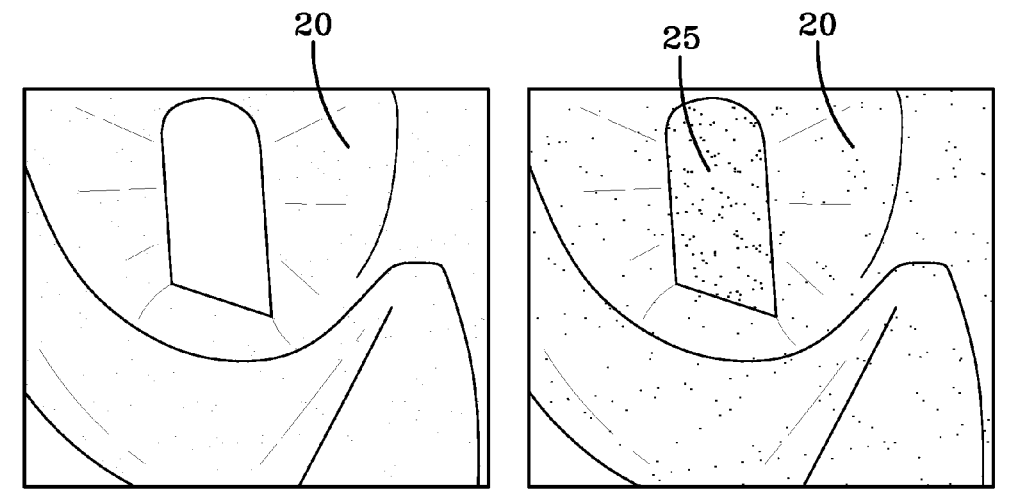
FIG. 2a depicts a portion of a cylinder head coolant passage in both an unblocked and completely blocked state.
Figure 2B:
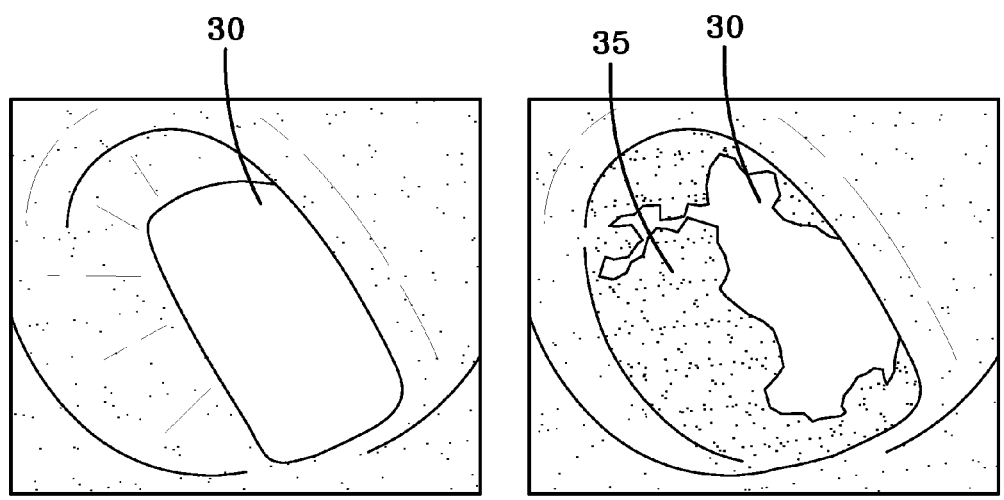
FIG. 2b depicts another portion of a cylinder head coolant passage in both an unblocked and partially blocked state.

The contrast between an open and unblocked coolant passage is dramatically illustrated in FIGS. 2a and 2b. In FIG. 2a, a completely unblocked internal section of a vehicle cylinder head coolant passage 20 is shown on the left, while the same section of the coolant passage with a complete blockage 25 thereof is shown on the right. Similarly, in FIG. 2b, a completely unblocked internal section of a vehicle cylinder head coolant passage 30 is shown on the left, while the same section of the coolant passage with approximately a 60% blockage 35 thereof is shown on the right. It can be easily understood from FIGS. 1-2 how such blockages can adversely affect the flow of coolant through associated coolant passages.

Figure 3:
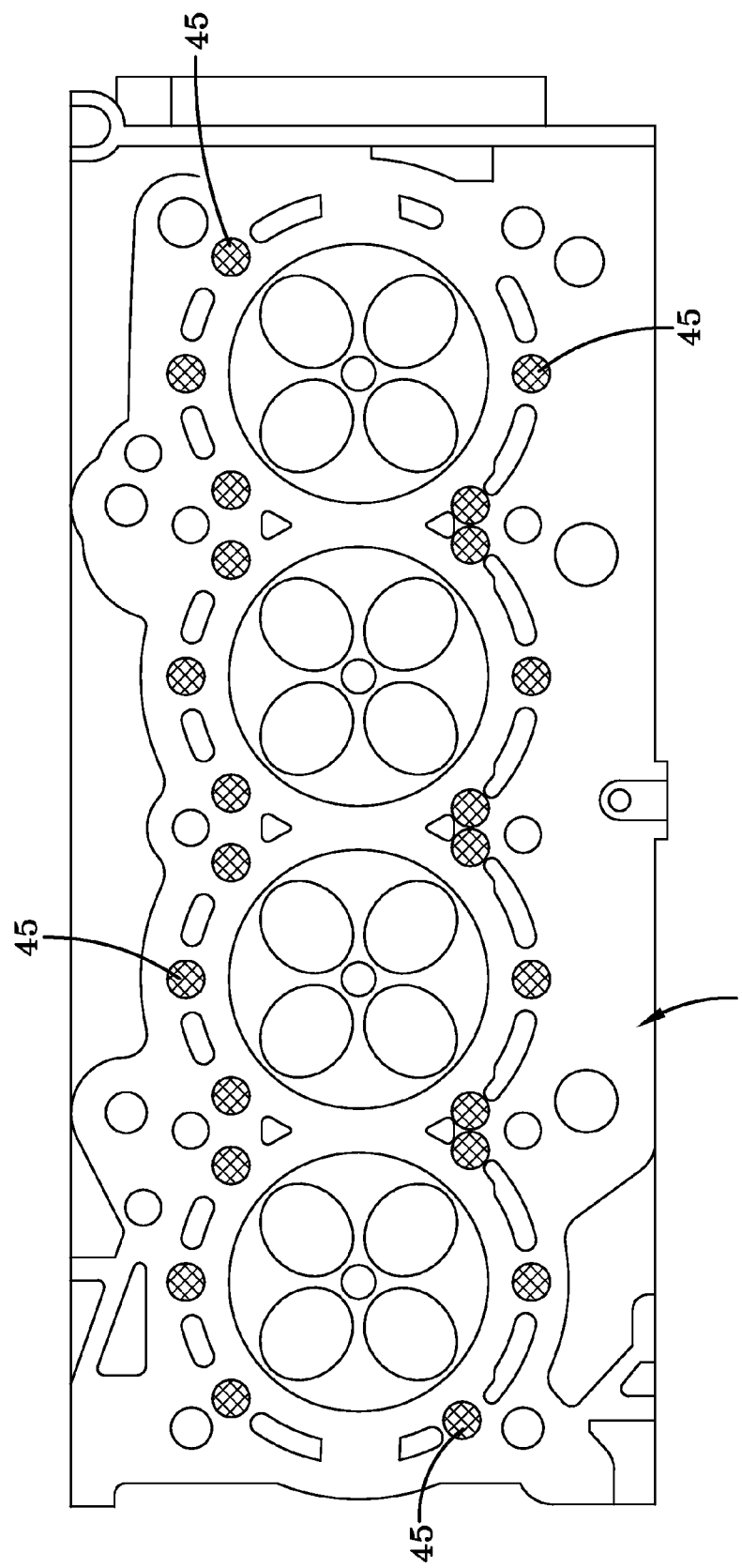
FIG. 3 is a bottom plan view of an exemplary vehicle cylinder head with its coolant passage entryways highlighted.

A bottom plan view of an exemplary vehicle cylinder head 40 is illustrated in FIG. 3. As shown, the side of the cylinder head 40 having the coolant passage entryways includes a mounting surface for mating with an engine block. This particular cylinder head 40 accommodates four cylinders (pistons), with four valves per cylinder. Obviously, however, virtually any cylinder head is subject to inspection by the present invention. A plurality of coolant passage entryways 45 are arranged around each piston location (as highlighted) and extend into the cylinder head 40. Inside the cylinder head, each coolant passage may have any number of tortuous paths. In any event, however, it is typically very difficult if not impossible to visually inspect the coolant passages at a point much beyond their entryway 45 at the bottom (mounting) surface of the cylinder head 40.

Figure 4A:
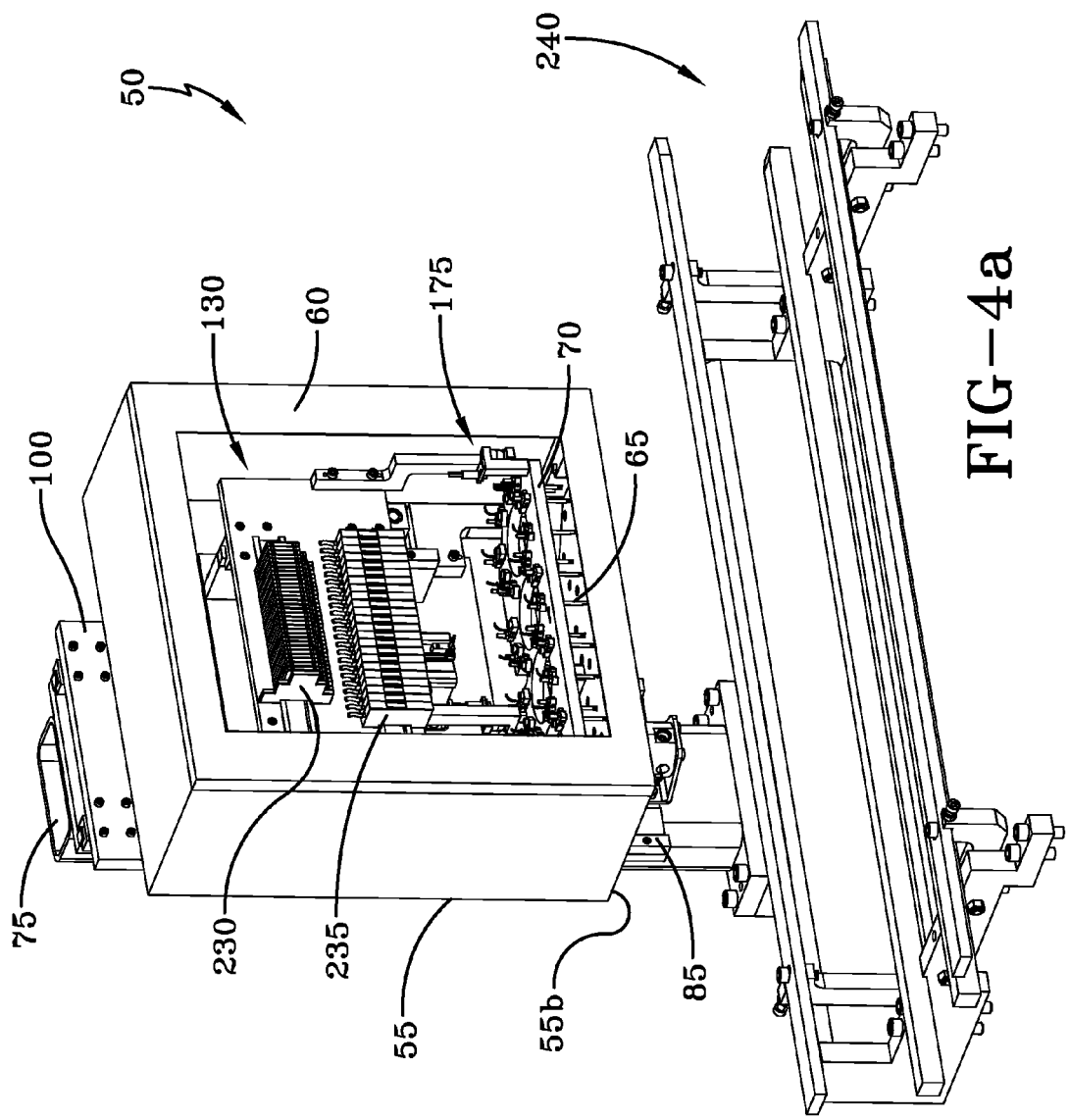

One exemplary embodiment of an assembled cylinder head coolant passage inspection device 50 (inspection device) of the present invention is shown in FIGS. 4a-4c. This inspection device 50 is designed for automated use, such as in conjunction with a portion of a cylinder head assembly or conveyor 240. Generally, the inspection device 50 includes a number of fiber-optic probes 60 that are associated with an enclosure 55 and adapted to be inserted and retracted into the coolant passages of a cylinder head (not shown) as it passes below on a conveyor 240.

As shown, the enclosure 55 preferably accommodates various components of the inspection device 50. Preferably, the enclosure 55 is adapted to contain at least the fiber-optic probes 65 and their associated mounting plate 70. The enclosure 55 may also accommodate various electronic components, such as connecting blocks 230 and/or fiber-optic sensor amplifiers 235. Apparatus for effecting extension/retraction of the fiber-optic probes is also preferably located within the enclosure 55. The enclosure is generally open, or partially open along a side from which the fiber-optic probes will be extended. In this embodiment, the enclosure 55 is open at its bottom 55b, but the open surface may be different in other embodiments. The enclosure 55 may also include a door 60 or other access panel, which may be of solid or partially open design.

This particular embodiment of the inspection device 50 employs dual stage motion to extend the fiber-optic probes 65 and insert the ends thereof into the coolant passages of a cylinder head. More specifically, in this particular embodiment, the enclosure 55 is moveably mounted with respect to the conveyor 240 and the fiber-optic probes 65 are moveably mounted with respect to the enclosure and the cylinder head.

As can be best observed in FIGS. 4a-4c and FIG. 5, the enclosure 55 is moveably mounted to frame 75 that extends from the conveyor 240, or a structure associated with the conveyor. The enclosure 55 is moveably mounted so that it can be moved toward and away from the conveyor 240 and a cylinder head located thereon. In this embodiment, movement of the enclosure 55 occurs in a vertical direction, but it should be realized that other orientations are also possible.

Movement of the enclosure 55 can be accomplished in various ways that would be understood by one skilled in the art. However, in this particular embodiment, movement of the enclosure 55 is accomplished by an enclosure motive assembly 78 that employs a pneumatic cylinder 80 (see FIGS. 4c and 5) motive device. A linear guide system, such as the linear guide rails 85 and corresponding guide blocks 90 are preferably provided to direct movement of the enclosure 55. A motion preventing device, such as the locking device 160 shown with respect to the fiber-optic probe assembly in FIG. 6, may be associated with the enclosure 55 to prevent movement thereof in the case of a power loss, etc.

Because cylinder heads may reach an inspection point prior to undergoing certain machining processes, it is possible that a cylinder head might be positioned on the conveyor such that the surface thereof containing the coolant passage entryways is not parallel to the bottom face 55b of the enclosure 55. As such, the inspection device 50 is designed to provide for self-alignment of the enclosure 55 with the mating surface of a cylinder head.

Figure 5:
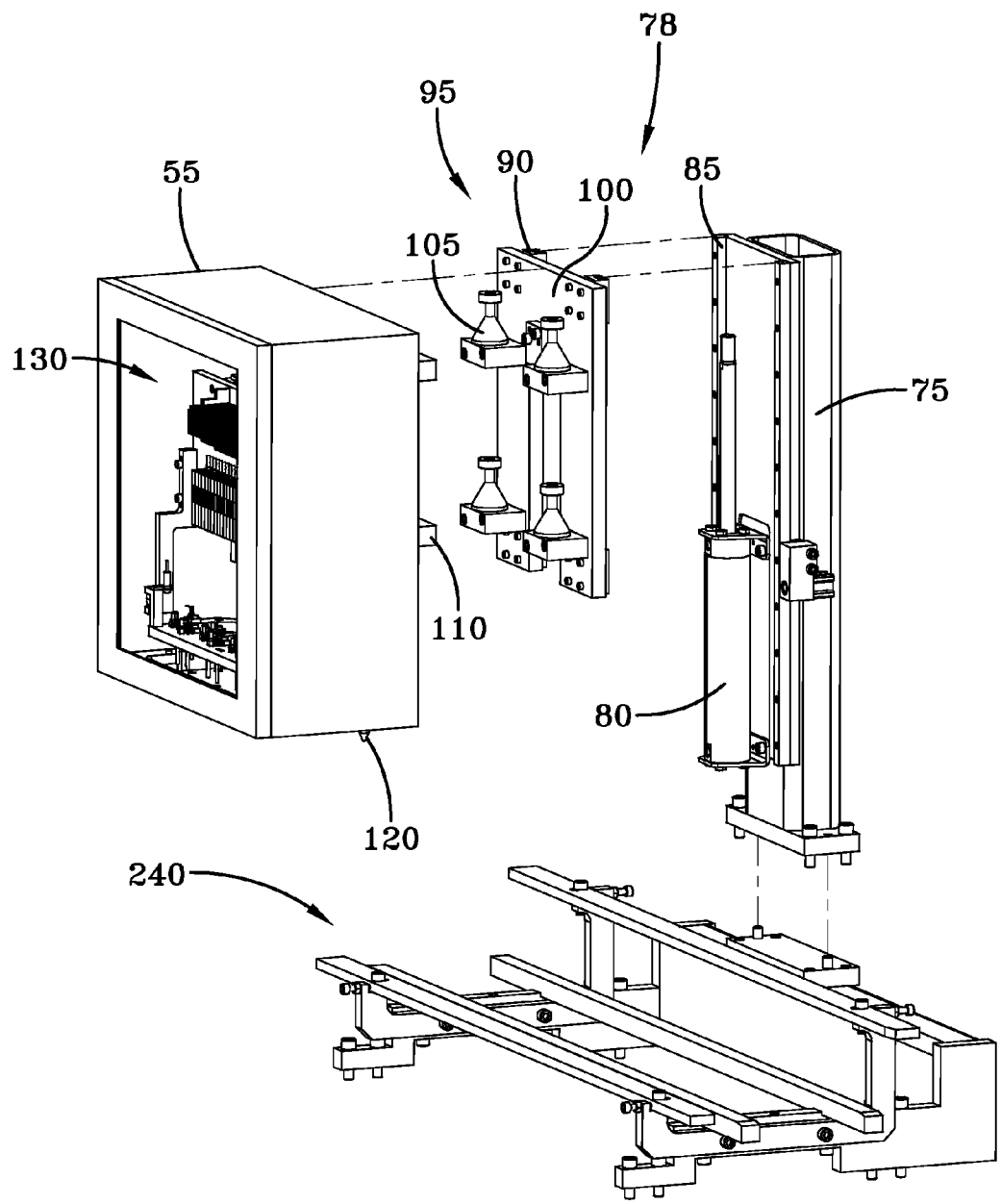
FIG. 5 is a partially exploded view of the device of FIGS. 4a-4c.

As can be best observed in FIG. 5, an intermediary mounting plate assembly 95 resides between the enclosure 55 and the pneumatic cylinder 80. The mounting plate assembly 95 functions to floatingly connect the enclosure 55 to the pneumatic cylinder 80 and linear guide system.

More particularly, the mounting plate assembly 95 includes at least a first mounting plate 100 having the guide blocks 90 attached to one side thereof, such that the mounting plate is moveable along the guide rails 85. To the opposite side of the mounting plate 100 is attached a number of substantially conical support elements 105. The support elements 105 are received by corresponding support brackets 110 that project from the rear of the enclosure 55. The support brackets 110 may be attached directly to the enclosure 55, or may be attached to a plate 115 or some other component that resides therebetween.

In any event, the support brackets 110 each include a thru-hole of a diameter sufficient to receive all or a portion of a corresponding one of the substantially conical support elements 105 when the enclosure is mounted to the mounting plate 100. It can therefore be understood that the enclosure 55 is supported by the mounting plate assembly 95 and is releasably retained by the substantially conical support elements 105.

During an inspection operation, the enclosure 55 is lowered by the pneumatic cylinder 80 into abutting contact with a mating surface of a cylinder head to be inspected. As can be understood, particularly in light of the foregoing description, the use of the substantially conical support elements 105 can be quite advantageous when locating the enclosure to the mating surface of the cylinder head. That is, the substantially conical support elements 105 allow the entire enclosure 55 to self-align with the mating surface of a cylinder head. Consequently, if the mating surface of a cylinder head is non-parallel to the bottom surface of the enclosure 55, the bottom surface of the enclosure can nonetheless be placed in mating contact therewith.

This is achieved by releasing the enclosure 55 from the support of the mounting plate assembly 95 upon its contact with the cylinder head. By continuing the downward movement of the pneumatic cylinder 80 after initial contact between the enclosure 55 and the cylinder head, the substantially conical support elements 105 are withdrawn (at least partially) from the corresponding support brackets 110 on the enclosure, and the enclosure is supported solely by the mating surface of the cylinder head. Subsequent upward vertical movement of the pneumatic cylinder 80 reengages the substantially conical support elements 105 with the thru-holes in the enclosure support brackets—even if the enclosure 55 is residing at a substantial angle or is otherwise some degree out of position on the cylinder head—and the enclosure is returned to its normal, supported position.

Preferably, one or more enclosure locating elements 120 are also employed to properly locate the enclosure 55 to a cylinder head. The enclosure locating elements 120 extend downward and below the bottom surface of the enclosure 55, and are arranged to engage corresponding features of the cylinder head. For example, the enclosure locating elements 120 may be locating pins that enter a corresponding aperture located in the mating surface of a cylinder head. The enclosure locating elements 120 may be attached directly to the enclosure 55 or to another component(s) that moves with the enclosure. The enclosure locating elements 120 help to ensure that the enclosure 55 is properly located to the cylinder head before the fiber-optic probes 65 are extended therefrom.

Proper positioning of the enclosure 55 on a cylinder head can be confirmed by the use of proximity sensors 125 or the like. As shown, a number of proximity sensors 125 are arranged along the bottom of the enclosure 55 to indicate proper contact between the bottom surface of the enclosure and the mating surface of a cylinder head. In this manner, it can be determined whether the enclosure 55 is properly positioned on the cylinder head. For example, if one or more of the enclosure locating elements 120 do not enter the corresponding apertures in the cylinder head because the cylinder head is too far out of proper position, the proximity sensors 125 will not be activated and the inspection process can be accordingly halted or aborted.

Figure 6:
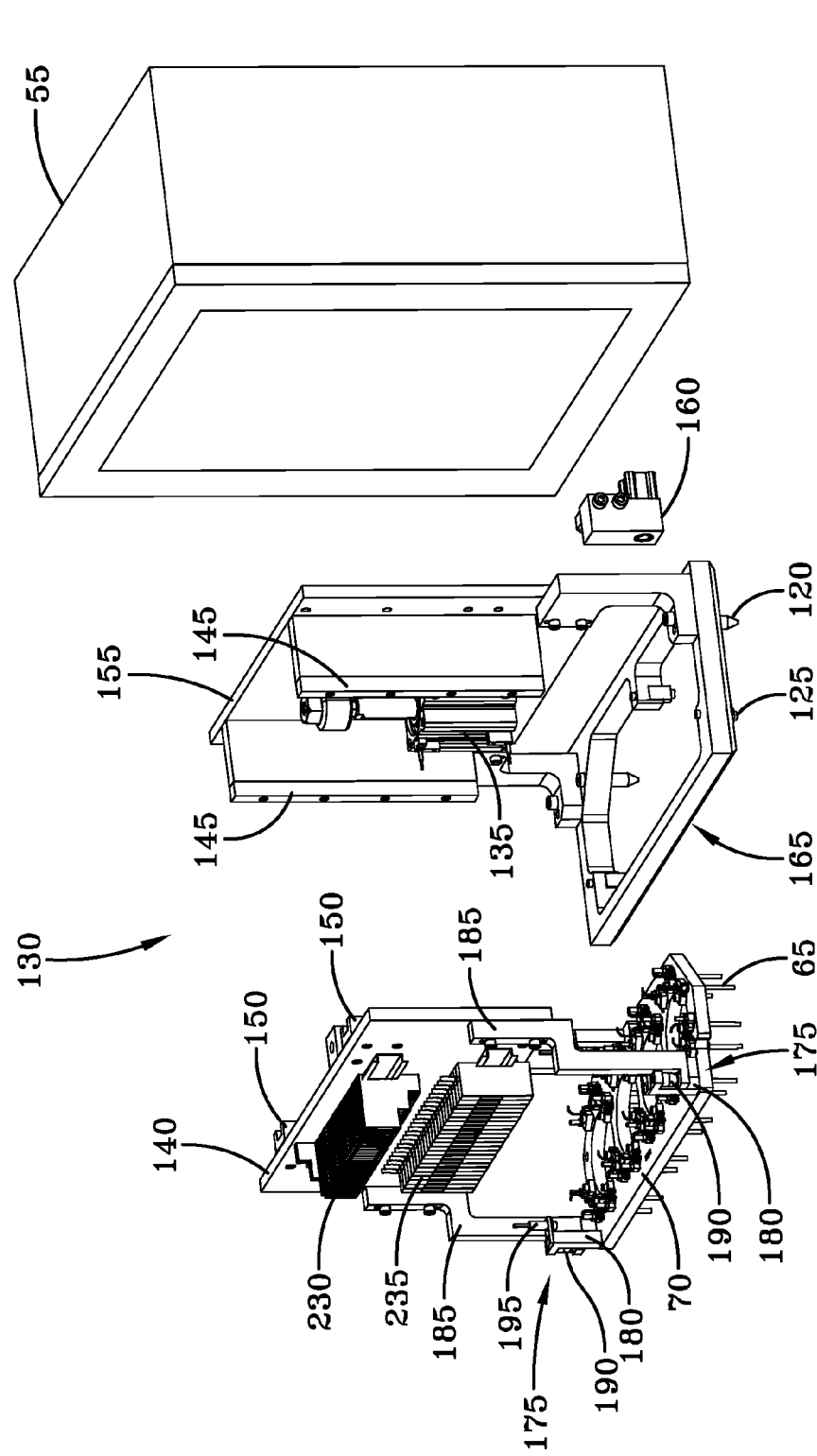
FIG. 6 is an enlarged and exploded view of a portion of the device of FIGS. 4a-4c.

Once proper positioning of the enclosure 55 on the cylinder head is confirmed, the fiber-optic probes 65 can be extended. Extension of the fiber-optic probes 65 is accomplished in this embodiment by means of a fiber-optic probe motive assembly 130. The fiber-optic probe motive assembly 130 can be seen to reside within the enclosure 55 in FIGS. 4a-4b and 5. An exploded view of the fiber-optic probe motive assembly 130 is shown in FIG. 6.

Figure 7:
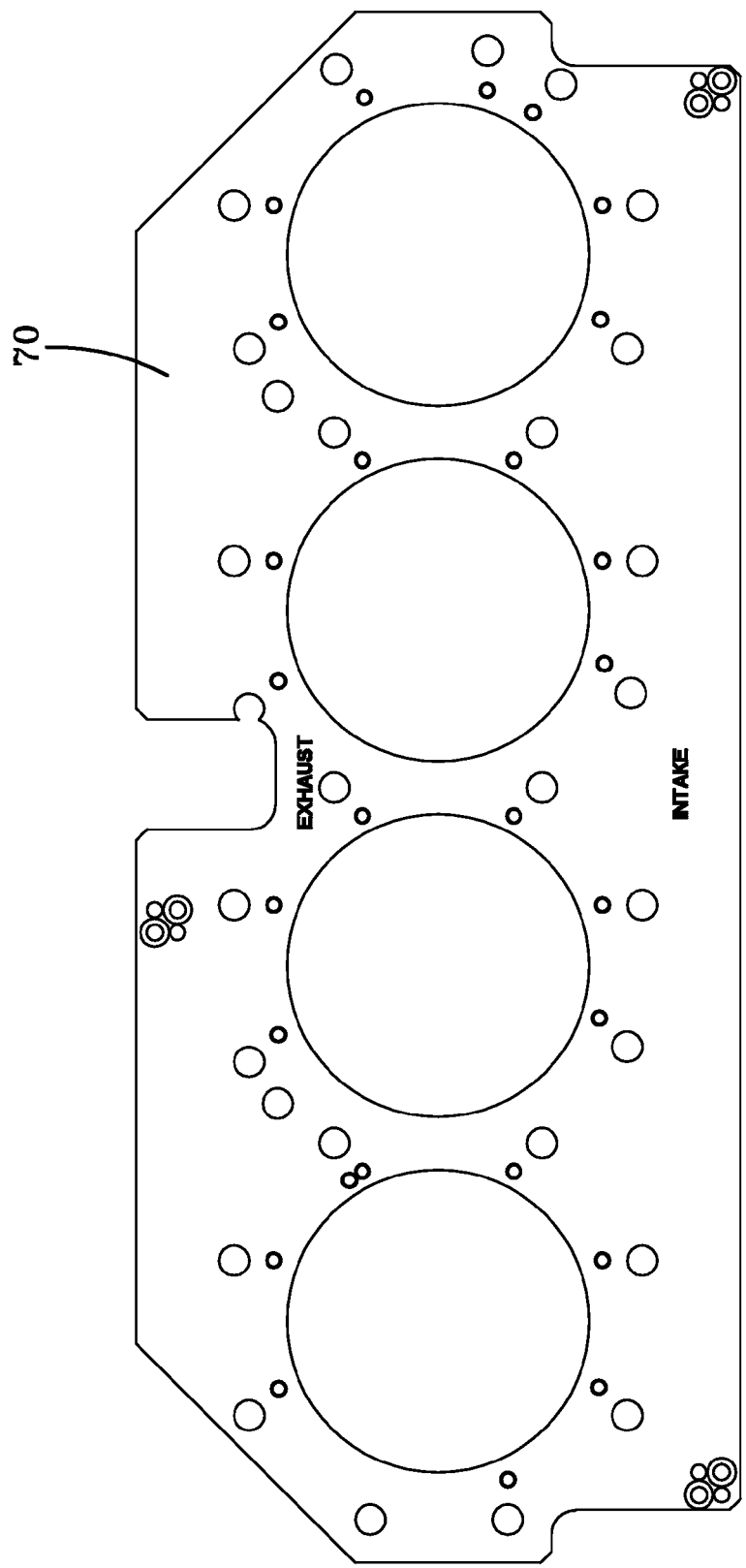
FIG. 7 is an enlarged top plan view of the mounting plate used to mount the fiber optic probes of the particular coolant passage inspection device of FIGS. 4a-4c.

As shown, the fiber-optic probe motive assembly 130 includes a number of fiber-optic probes 65 installed to the probe mounting plate 70. The probe mounting plate 70, which can be seen in more detail in FIG. 7, functions to retain the fiber-optic probes 65 in an arrangement that coincides with the arrangement of coolant passage entryways of a cylinder head to be inspected. The probe mounting plate 70 is movably mounted within the enclosure 55 so that the fiber-optic probes 65 are extendible and retractable with respect to a cylinder head to be inspected.

In this particular embodiment, extension and retraction of the fiber-optic probes 65 is accomplished by associating the probe mounting plate 70 of the fiber-optic probe motive assembly 130 with a pneumatic cylinder 135. More particularly, the probe mounting plate 70 is supported by a slidable mounting plate 140 that is connected to the pneumatic cylinder 135. In similar fashion to that described above with respect to movement of the enclosure 55, movement of the probe mounting plate 70 and the fiber-optic probes 65 is preferably directed by a linear guide system. This embodiment makes use of linear guide rails 145 and corresponding guide blocks 150 for this purpose. The linear guide rails 145, like the pneumatic cylinder 135, may be mounted to an interior wall of the enclosure 55, or may be mounted to an intermediary mounting plate 155 as shown. The guide blocks 150 are mounted to the appropriate side of the slidable mounting plate 140. As with the enclosure 55 a movement preventing device, such as the locking device 160 shown, may also be associated with the moveable fiber-optic probe assembly 130 to prevent movement thereof in the case of a power loss, etc.

An optional support frame 165 may be present along the bottom 55b wall of the enclosure 55. The support frame 165 may be connected to the intermediary mounting plate 155 as shown, or may be attached only to the enclosure 55. The support frame 165 may be used to add strength and/or rigidity to the enclosure 55 and/or to other components housed therein. In this embodiment, the support frame 165 forms the surface that will mate with and support the enclosure 55 on a cylinder head to be inspected. In other embodiments, the support frame 165 may act to reinforce a mating surface portion of the enclosure 55. To this end, at least certain ones of the enclosure locating elements 120 and proximity sensors 125 mentioned above may be affixed to and extend from the support frame 165 through associated apertures in the bottom wall 55b of the enclosure 55.

Figure 8:
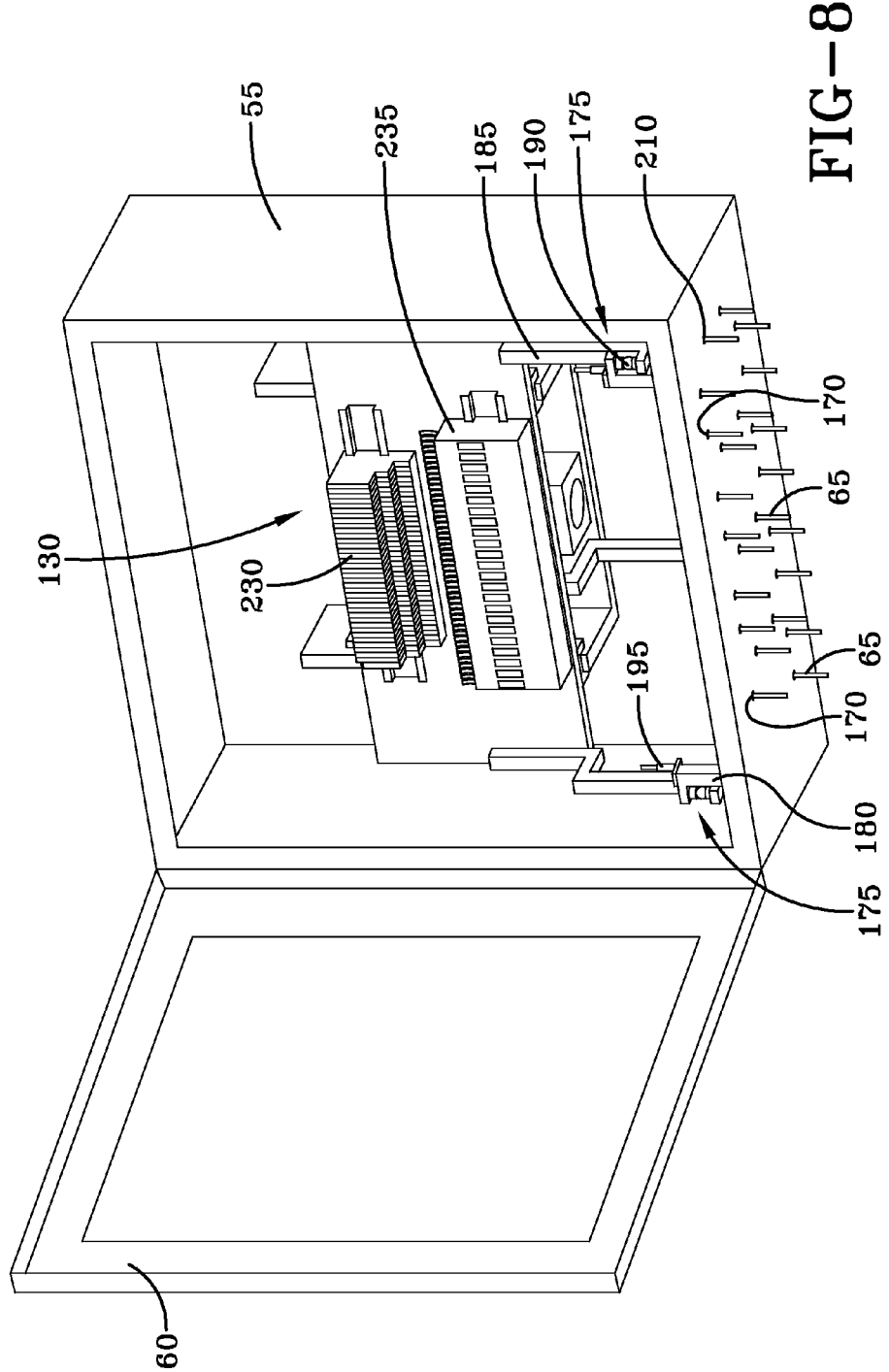
FIG. 8 is a detailed view of one exemplary embodiment of a fiber-optic probe assembly that can be used with a device of the present invention.

In operation, extension/retraction of the fiber-optic probes 65 occurs only after it has been confirmed that the enclosure 55 is properly mated to a cylinder head to be inspected (as described above). Subsequently thereto, the pneumatic cylinder 135 is activated to extend the probe mounting plate 70 and associated fiber-optic probes 65. As illustrated in FIG. 8, the fiber-optic probes 65 are thereby extended through corresponding probe apertures 170 located in the bottom wall 55b of the enclosure 55. The fiber-optic probes 65 are extended by some predetermined amount that permits sufficient entry thereof into the cylinder head coolant passages to be inspected. Upon completion of the inspection process or at some time prior thereto, the fiber-optic probes 65 are retracted by the pneumatic cylinder 135. Preferably, the fiber-optic probes 65 are retracted to a position internal to the enclosure 55.

In order to further ensure proper alignment between the fiber-optic probe motive assembly 130 and the coolant passages of a cylinder head, and to minimize any damage to the fiber-optic probes 65, this particular embodiment of the inspection device 50 also includes a floating probe mounting plate arrangement 175 (see FIGS. 4a, 6 and 8). In this embodiment, the floating probe mounting plate arrangement 175 is accomplished by employing three probe mounting plate support arms 180 to suspend the probe mounting plate 70 from corresponding slidable mounting plate support arms 185. Other numbers of support arms may, of course, be present.

Preferably, the probe mounting plate support arms 180 and slidable mounting plate support arms 185 have corresponding end portions that permit the a tooling ball 190 or similar element to be located therebetween. The tooling ball 190 facilitates separation of the support arms 180, 185. A proximity detector 195 or similar sensor is also preferably located near one or all of the tooling balls 190.

In operation, sufficient contact between one or more of the fiber-optic probes 65 and a cylinder head to be inspected will cause an upward displacement of the probe mounting plate 70. If the upward displacement of the probe mounting plate 70 exceeds some predetermined amount, the proximity sensor 195 will send a signal to an associated processor and movement of the probe mounting plate will be halted or reversed. As such, damage to the fiber-optic probes 65 as a result of their contact with a cylinder head can be minimized or prevented.

The number and location of the fiber-optic probes 65 may vary. Preferably, the number and location of fiber-optic probes 65 corresponds to the number and location of coolant passage entryways present on the cylinder head to be inspected. In this manner, a fiber-optic probe 65 can be inserted into each coolant passage substantially simultaneously and inspection thereof can be carried out without the need to withdraw and reinsert the probes. The fiber-optic probes 65 can be keyed or otherwise fixed in the probe mounting plate 70 to prevent their rotation and to ensure that the fiber-optic probes will be properly oriented for viewing of their associated coolant passages during the inspection process.

Figure 9:
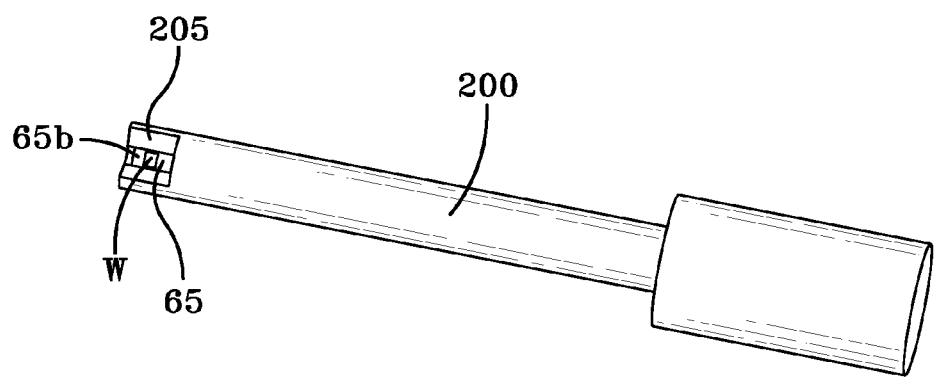
FIG. 9 illustrates a portion of the device of FIGS. 4a-4c, wherein the fiber-optic probes are shown in an extended (inspection) position.

While various fiber-optic probe designs may be used with the present invention, one particularly useable embodiment of such a fiber-optic probe 65 is depicted in FIG. 9. As can be seen, this particular fiber-optic probe 65 includes a protective housing 200 that substantially surrounds the probe shaft. Preferably, the protective housing 200 extends substantially to the distal end 65b of the fiber optic probe 65, so as to protect it from damage during extension into and/or inspection of an associated cylinder head coolant passage. In such an embodiment, the protective housing 200 includes a cutout or aperture 205 around the light emitting/receiving window W of the fiber-optic probe 65. Alternatively, if present, a protective housing may stop short of the light emitting/receiving window W of the fiber-optic probe 65.

The inspection device 50 may be provided with various other features in order to further protect the fiber-optic probes 65 from damage or malfunction due to contamination. For example, a wiper element 210 may be present at an exterior and/or interior side of each fiber-optic probe aperture. Such wiper elements 210 can function to wipe away any contamination present on any exposed outer surfaces of the fiber-optic probes 65 or the protective housings 200 associated therewith. In lieu of, or in addition to the use of wiper elements, the enclosure 55 may be pressurized to minimize or prevent the intrusion of contamination.

Figure 10:
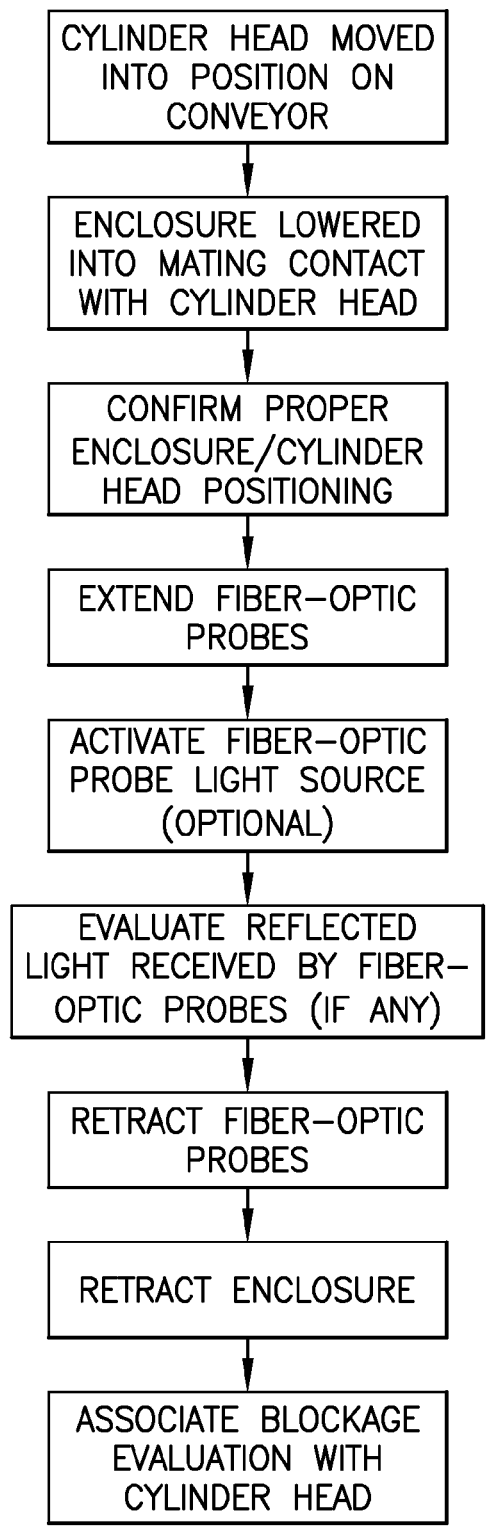
FIG. 10 is a schematic diagram describing one possible mode of operation for the exemplary embodiment of the device of FIGS. 4a-4c.

In conjunction with the foregoing description, operation of the inspection device 50 can be better understood by reference to the flowchart of FIG. 10. As previously described, a cylinder head (not shown) is first moved into an inspection position on the conveyor 240. With the cylinder head properly positioned, the enclosure 55 is lowered until it makes contact with and is supported on a mating surface of the cylinder head. If the enclosure 55 mates properly with the cylinder head, a signal indicative of such is sent to an associated processor, and the inspection process continues as described below.

If the enclosure 55 does not mate properly with the cylinder head, a signal indicative of such is sent to the associated processor and the inspection process is aborted or reinitiated. In the latter case, the enclosure 55 is generally retracted to or near its stored position and subsequently re-contacted with the cylinder head. This process may be repeated several times until the enclosure 55 is properly positioned or it is determined that proper positioning thereof is impossible. If proper positioning of the enclosure 55 is deemed impossible, an operator may be alerted, etc.

Once the enclosure 55 is properly positioned on the cylinder head, the fiber-optic probes 65 are extended in the manner previously described. The fiber-optic probes 65 enter their corresponding coolant passages and emit light therein. In one embodiment, light is continually emitted by the fiber-optic probes 65, but analysis is conducted only when the probes are positioned within coolant passages to be inspected. In an alternative embodiment, an associated fiber-optic probe light source(s) may be turned on only when the fiber-optic probes 65 are extended.

With the fiber-optic probes 65 extended into the coolant passages to be inspected, light is emitted thereto, and reflected light is received by the fiber-optic probes and subsequently analyzed. As is described in more detail below with respect to FIGS. 11a-11b, if no reflected light is detected or the amount of detected light is below some threshold value, the associated coolant passage(s) is deemed to be in acceptable condition with respect to blockages. Contrarily, if reflected light is detected in an amount that exceeds some threshold value, the associated coolant passage(s) is are deemed to contain an unacceptable blockage(s).

Upon completion of the foregoing analysis or at some point after the fiber-optic probes 65 have completed emitting and, if present, receiving reflected light, the fiber-optic probes are retracted as previously described. The enclosure 55 is then retracted to the stored position as illustrated in FIGS. 4a-4c. The blockage evaluation resulting from the inspection process is then associated with the inspected cylinder head.

Disposition of an inspected cylinder head will typically depend on the results of the inspection process. For example, if the inspection process indicates no blockages, or the presence of an acceptably small blockage(s), the cylinder head may be transferred to the next processing or assembly stage of the manufacturing process. If the inspection process indicates the presence of an unacceptable blockage(s), the cylinder head may be flagged for additional offline inspection or may be transferred to a scrap area. Other outcomes are, of course, also possible.

Figure 11A:
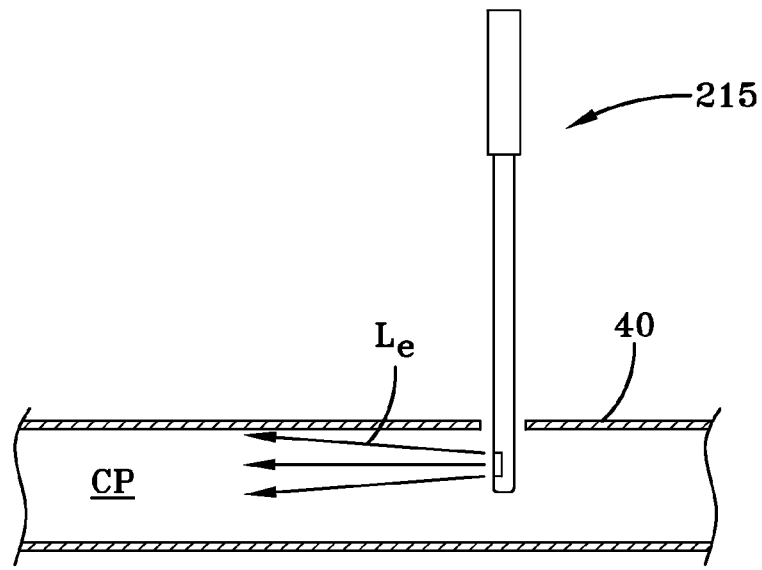
FIG. 11a illustrates light from a fiber-optic probe of the present invention being transmitted through an unblocked coolant passage.
Figure 11B:
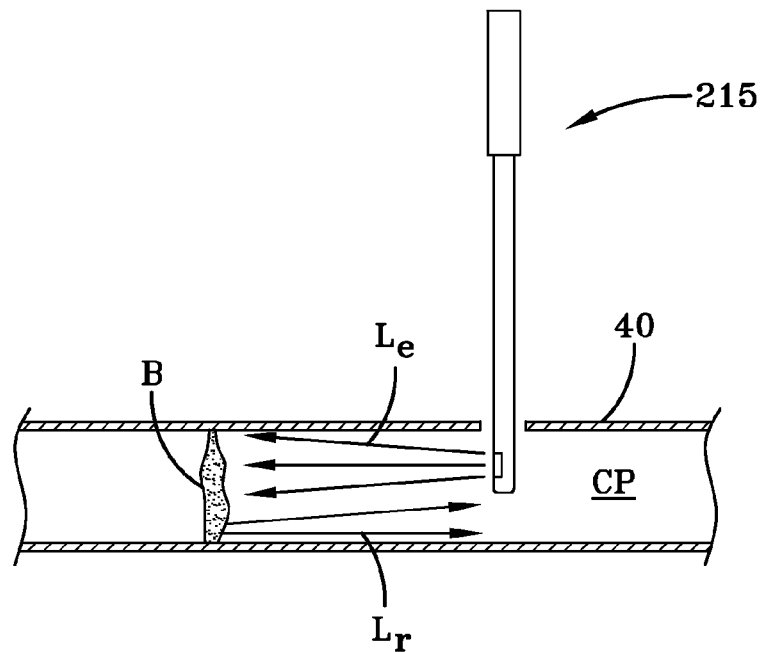
FIG. 11b illustrates light from a fiber-optic probe of the present invention being reflected off of a blockage in a coolant passage and received back at the fiber-optic probe.

A more detailed view of an exemplary fiber-optic probe 215 of the present invention after extension thereof into a coolant passage CP can be observed in FIGS. 11a-11b. FIG. 11a depicts the scenario wherein the fiber-optic probe 215 has been inserted into a coolant passage CP having no blockage, or a blockage of such diminutive size so as to be undetectable. As can be seen in this case, emitted light $L_e$ from the fiber-optic probe 215 passes through the coolant passage CP without being reflected back to the fiber-optic probe. Thus, an unblocked coolant passage is indicated.

A contrary situation is depicted in FIG. 11b. In this case, the fiber-optic probe 215 has been inserted into a coolant passage CP having a detectable blockage B (which may be far less substantial in reality than the illustrated blockage). As such, emitted light $L_e$ from the fiber-optic probe 215 strikes the blockage B and becomes reflected light $L_r$ that travels back to the probe. The fiber-optic probe 215 receives the reflected light $L_r$ and transmits it to a sensor (not shown), such as a photodetector or some other suitable device that is capable of evaluating the reflected light to determine, in conjunction with a processor, the presence and/or size of a blockage.

Generally, if the magnitude of the reflected light $L_r$ exceeds some threshold value associated with the sensor, the presence of a blockage will be indicated. Threshold values may be calculated, determined experimentally, etc. The threshold values may be set such that only blockages of a certain size will reflect enough light to cause a device/system of the present invention to indicate that there is a problem. In this manner, cylinder heads with a coolant passage(s) containing a blockage(s) small enough not to negatively affect operation can be allowed to pass inspection. Alternatively, any blockage of sufficient size to be detectable using a fiber-optic probe 215 and sensor of the present invention can be made to set off an alarm or otherwise make its presence known.

As mentioned above, various actions can be caused to occur upon the detection of a blockage(s). For example, a device and method of the present invention can alert an operator to the presence of a blockage(s) and/or otherwise mark an associated cylinder head with such an indicator. A device and method of the present invention may also function to trigger other equipment to remove the cylinder head from the manufacturing process or to prevent the operation of a downstream process to be performed on the cylinder head.

Figure 12A:
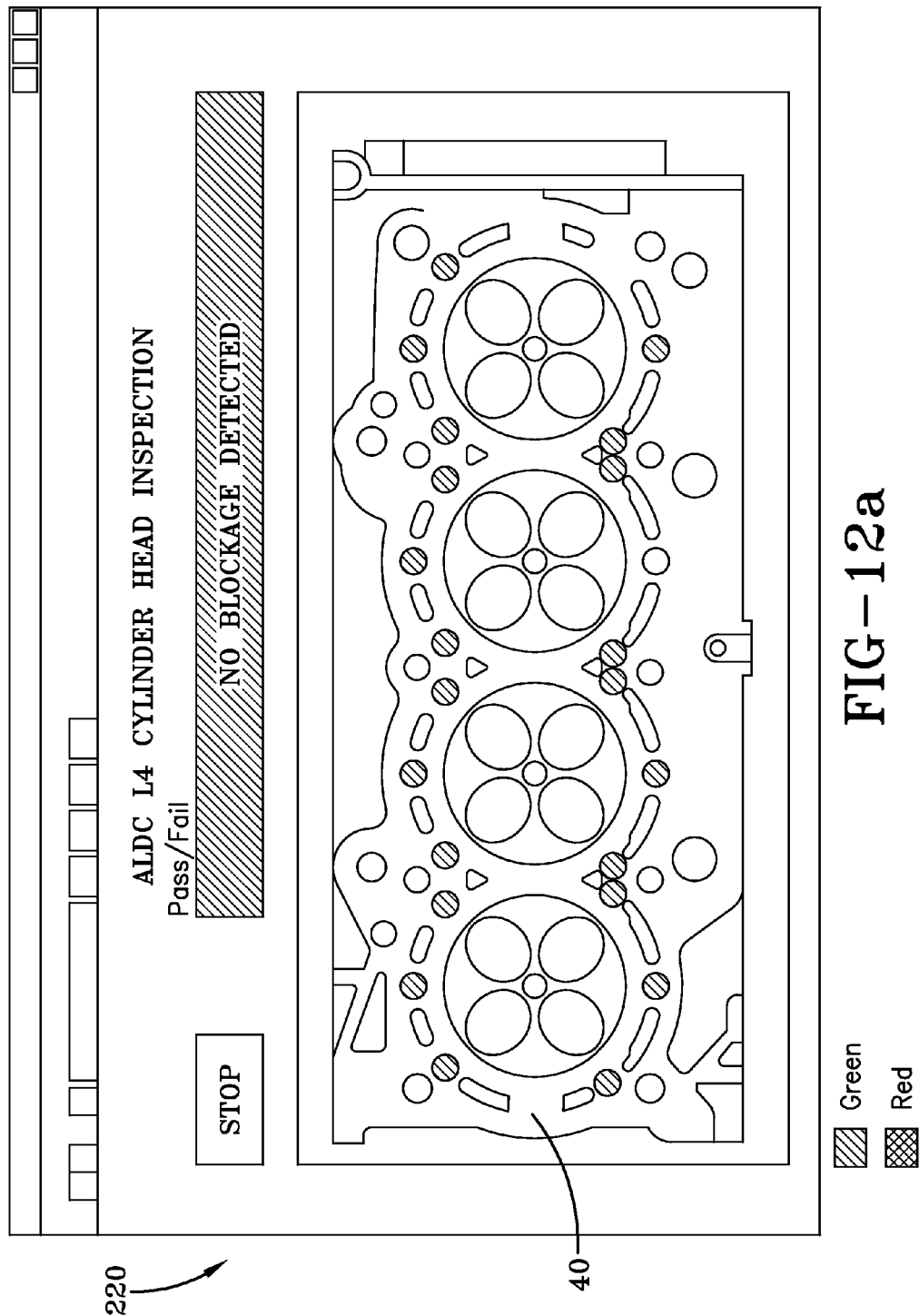
FIGS. 12a and 12b depict an exemplary embodiment of a monitoring system display of the present invention, wherein a cylinder head with unblocked coolant passages and a cylinder head with a blocked coolant passage are being respectively inspected.
Figure 12B:
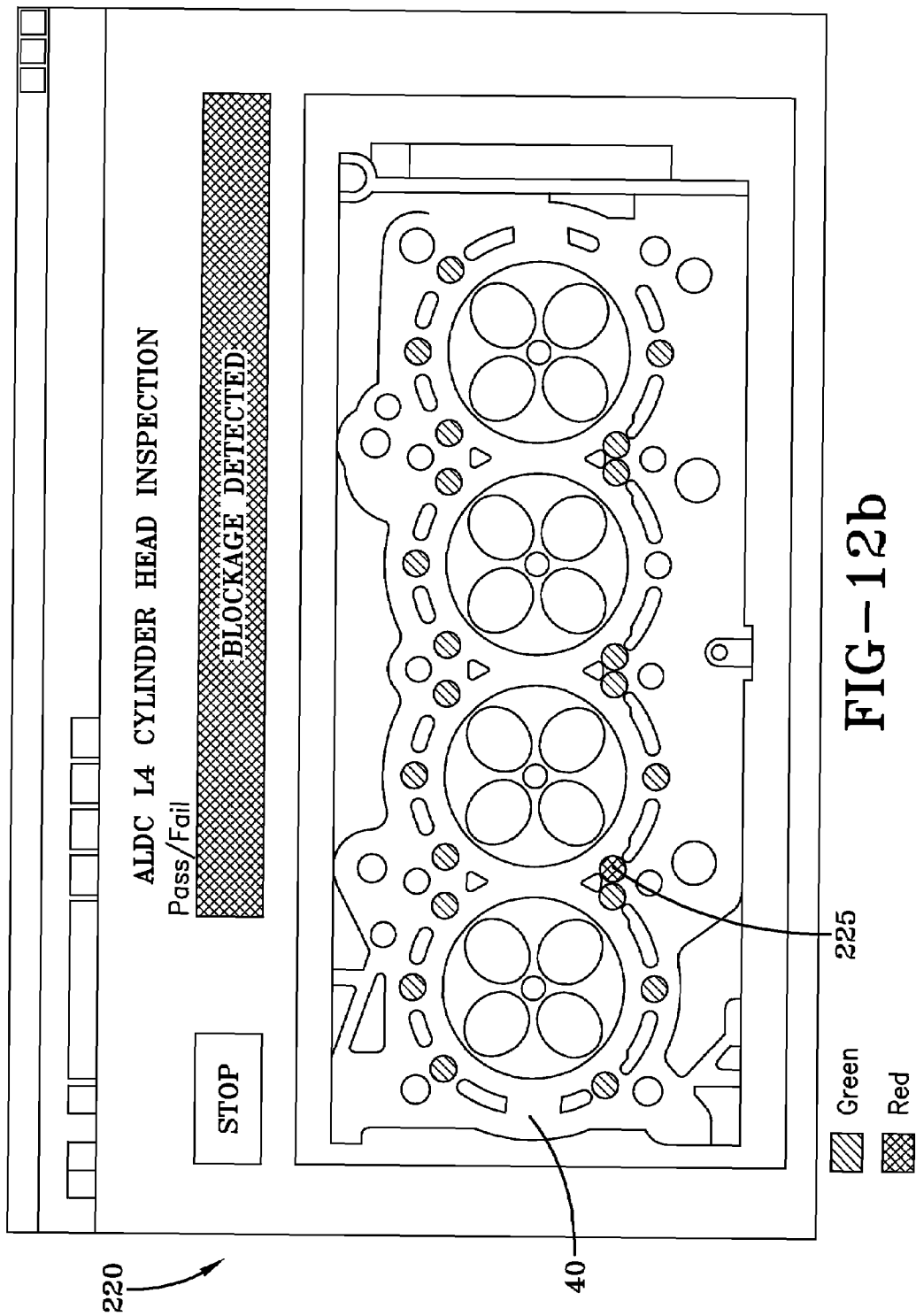

Preferably, but not necessarily, a monitoring portion of the present invention indicates the presence of, and optionally, the relative location of, a blockage(s). As shown in FIGS. 12a-12b, such an indication is accomplished graphically in one embodiment of the present invention.

As can be seen in FIGS. 12a-12b, the present invention may include a display 220 for transmitting a view(s) of a cylinder head 40 being inspected (or a likeness thereof). In FIG. 12a, it is indicated both graphically (e.g., by the green color of all the highlighted coolant passage entryways) and in writing that the cylinder head inspection process found no coolant passage blockages.

In the contrary scenario of FIG. 12b, it is indicated both graphically (e.g., by changing the color of the highlighting associated with a blocked coolant passage entryways) and in writing that the cylinder head inspection process found a coolant passage blockage. In addition to the presence of a blockage, the general location of the blockage 225 is also indicated on the cylinder head image by the (e.g., red) changed highlighting color associated with the entryway of the blocked coolant passage.

Obviously, a variety of other methods of alerting an operator to the presence and/or location of a coolant passage blockage(s) are also possible, and the aforementioned example is not meant to limit the present invention in any way. Alternatives are possible even with the aforementioned embodiment of FIGS. 12a-12b. For example, different highlighting colors could obviously be used, or highlighting could be used only to indicate a blocked or unblocked coolant passage.

The display 220 may be an integral part of a computer or may be driven by a computer or other processing device. Software necessary to initialize, operate or otherwise interact with the fiber-optic probes, and to provide the desired alerts and/or views of the cylinder head, etc., may be associated with the computer or other processor. Preferably, a graphical user interface (GUI) is associated with any such software to allow for interaction therewith by an operator.

Other functions may also be associated with such software. For example, software may make it possible to track or otherwise retain data relating to blockages. Various means are also available to associate a cylinder head with the mold used to create it. As such, it is further contemplated that if data from one or more inspection devices of the present invention indicates a repeating problem with one or more cylinder head coolant passages associated with a particular mold, the inspection device(s) may signal the associated casting machine to activate an alarm, halt the casting process, etc. An inspection device of the present invention can be placed in wired or wireless communication with one or more casting machines for this purpose. Therefore, data from an inspection device of the present invention can be related to specific casting molds, casting machines, etc. Such data may be stored in one or more databases that are internal or external to a computer or other processor associated with the inspection device.

In order to enable the inspection of a maximum variety of cylinder heads, the inspection device 50 and other inspection device embodiments of the present invention can be provided with certain features that make it easily interchangeable. For example, in addition to the use of the conical support elements that enable the entire enclosure to be released from its associated motive apparatus, the enclosure may be equipped with handles or other similar elements that facilitate its removal—whether by hand or by other devices or equipment. In addition, any electrical or pneumatic connections may be designed with quick-change connectors, etc., that also facilitate removal of the enclosure. As such, if it is desired to inspect a cylinder head that has a coolant passage arrangement dissimilar to the current arrangement of fiber-optic probes of the installed inspection device, the current enclosure and its associated components can be removed and replaced with another enclosure having properly arranged fiber-optic probes.

In another embodiment of the present invention, a plurality of inspection devices may be provided along a conveyor or at a different location to effectuate inspection of dissimilar cylinder heads. For example, assuming that there is sufficient space, a number of inspection devices like the inspection device 50 of FIGS. 4a-4c may be arranged along the conveyor 240. Each inspection device may be associated with a particular cylinder head or number of cylinder heads. The conveyor can then be equipped with different cylinder head stopping/locating points so that a given cylinder head will always be located to its corresponding inspection device. Such an arrangement may also be placed in an offline inspection area, etc., so as to make an offline inspection process as efficient as possible.

Various other embodiments of an inspection device of the present invention and its method of use are possible. For example, instead of the enclosure and displacement apparatus discussed above, a number of fiber-optic probes may be moved to and from cylinder heads to be inspected by a robot. In such an embodiment, the robot may be connected with a fiber-optic mounting plate that is similar or dissimilar to the probe mounting plate 70 shown herein and described above. When a robot is employed, it may be associated with a quick-change tool changer that allows the robot to quickly change between various fiber-optic probe assemblies. Such tool changers would be well known to one skilled in the art and, therefore, need not be described in detail herein. Such an embodiment would be well-suited to an inspection process wherein more than one variety of cylinder head is to be inspected.

When a robot or other flexible motive means is used, an inspection device of the present invention can also have a fewer (or greater) number of fiber-optic probes than the number of coolant passages present in a cylinder head to be inspected. In the former case, the fiber-optic probes are simply withdrawn after inspection of a like number of coolant passages, moved to a new location along the cylinder head, and inserted into additional cooling passages where the inspection thereof subsequently takes place. This process is repeated until all the cooling passages of interest have been inspected. In the latter case, the fiber-optic probes must be arranged in a manner so as to correspond with coolant passages to be inspected, and also so that any extra probes do not contact obstructions during the inspection operation. Alternatively, the extra probes may be made to be removable.

An inspection device and method of the present invention can be used in various ways. In a simplistic embodiment, a device and method of the present invention may be located away from an assembly line or other manufacturing area, such as in an inspection or quality control area. In such an embodiment, a device of the present invention can be used to perform off-line inspection of cylinder head coolant passages. Inspections conducted in this manner need not generally be completed within a time frame established by the cylinder head manufacturing process. As such, it is contemplated that an inspection device of such an embodiment may be automated, or may be operated by hand.

In an alternate embodiment, such as that shown herein and described above, an inspection device and method of the present invention may be located at an assembly line or other manufacturing area. In such an embodiment, a device of the present invention can be used to perform on-line inspection of cylinder head coolant passages in real time during the manufacturing process. Since inspections conducted in this manner will typically need to be completed within a time frame established by the cylinder head manufacturing process, it is preferable, but not essential, that operation of an inspection device of such an embodiment be automated.

An inspection device and/or the software and processor mentioned above may also be in communication with an assembly line or some other equipment associated with cylinder head manufacture to ensure that coolant passage inspection is timely initiated and terminated. In such an embodiment, it is possible for an operator to be involved with the inspection process only when a problem is found (or not at all if an automated means for dealing with rejected cylinder heads is provided).

Therefore, it can be understood from the foregoing description that an inspection device and method of the present invention can be used to quickly and easily determine whether a blockage(s) is present in one or more vehicle cylinder head coolant passages—regardless of the type of cylinder head involved or the number of coolant passages present. A device and method of the present invention can be used by hand, or can be automated. A device and method of the present invention can be used directly at the site of manufacture, or can be used off-line. Therefore, while certain embodiments of the present invention are described in detail above, the scope of the invention is not to be considered limited by such disclosure, and modifications are possible without departing from the spirit of the invention as evidenced by the following claims:

What is claimed is:

1. A device for detecting a blockage within a coolant passage of a vehicle cylinder head, comprising:
    at least one fiber-optic probe for emitting and receiving light;
    a means for inserting said at least one fiber-optic probe into and withdrawing said at least one fiber-optic probe from a coolant passage to be inspected; and
    a sensor in communication with said at least one fiber-optic probe, said sensor operable to register emitted light that may be reflected back to and received by said at least one fiber-optic probe;
    wherein, a blockage in said coolant passage is deemed present when an amount of reflected light registered by said sensor exceeds some threshold level.

2. The device of claim 1, wherein a plurality of fiber-optic probes are present and are used simultaneously to inspect a plurality of coolant passages.

3. The device of claim 1, wherein said at least one fiber-optic probe is manually inserted into and withdrawn from a coolant passage to be inspected.

4. The device of claim 1, wherein said at least one fiber-optic probe is inserted into and withdrawn from a coolant passage to be inspected by a motive device selected from the group consisting of an electro-mechanical cylinder, a pneumatic cylinder, a hydraulic cylinder, and a robot.

5. The device of claim 1, further comprising an enclosure for housing at least said at least one fiber-optic probe, said at least one fiber-optic probe extending through a corresponding aperture(s) in said enclosure when in an inspection position.

6. The device of claim 5, wherein said enclosure is moveable toward and away from a cylinder head to be inspected.

7. The device of claim 6, wherein said enclosure is floatingly suspended by a motive assembly such that said enclosure can self-align with a mating surface of said cylinder head to be inspected upon contact therewith.

8. The device of claim 5, wherein said at least one fiber-optic probe is moveable within said enclosure toward and away from a cylinder head to be inspected.

9. The device of claim 5, further comprising at least one locating element for locating said enclosure on said cylinder head.

10. The device of claim 1, further comprising a protective housing that substantially surrounds said at least one fiber-optic probe to protect it from damage during its insertion into said coolant passage.

11. The device of claim 1, further comprising a display for indicating the presence of a blockage.

12. The device of claim 11, wherein the relative location of said blockage(s) is indicated on said display.

13. A device for detecting the presence of blockages within multiple coolant passages of a vehicle cylinder head, comprising:
    a moveable enclosure;
    a plurality of light emitting/receiving fiber-optic probes retained in a fixed arrangement by a probe mounting plate, said fiber-optic probes located at least substantially within said housing when in a non-inspection position;
    a first motive assembly for moving said enclosure into contact with and withdrawing said enclosure from a mating surface of a cylinder head to be inspected;
    a second motive assembly located within said enclosure and operative to cause the insertion and withdrawal of said fiber-optic probes to/from coolant passages of said cylinder head to be inspected, said fiber-optic probes extending through corresponding fiber-optic probe apertures in said enclosure when in an inspection position;

at least one sensor in communication with said fiber-optic probes, said at least one sensor operable to register emitted light that may be reflected back to and received by said fiber-optic probes during inspection of said coolant passages; and a processor in communication with said at least one sensor, said processor operative to compare any reflected light readings registered by said sensor to a threshold value to determine if any blockages are present within the coolant passages of said cylinder head to be inspected.

14. The device of claim 13, wherein the number of fiber-optic probes used is equivalent to the number of coolant passage entryways present in said cylinder head to be inspected.

15. The device of claim 13, wherein said probe mounting plate is suspended within said enclosure such that sufficient contact between one or more of said fiber-optic probes and said cylinder head to be inspected will displace said probe mounting plate.

16. The device of claim 15, further comprising one or more sensors associated with said probe mounting plate and operative to signal an associated processor if said probe mounting plate is so displaced.

17. The device of claim 16, wherein extension of said fiber-optic probes is halted or said fiber-optic probes are retracted as a result of a signal from said one or more sensors.

18. The device of claim 13, wherein said enclosure is floatingly mounted with respect to its associated motive assembly such that said enclosure can self-align with a mating surface of said cylinder head to be inspected upon contact therewith.

19. The device of claim 18, wherein said enclosure is mounted to its associated motive assembly using a plurality of substantially conically shaped locating elements that are received in apertures of corresponding locating brackets, said substantially conically shaped locating elements being at least partially withdrawn from said locating elements upon contact between said enclosure and said cylinder head to be inspected.

20. The device of claim 13, further comprising at least one locating element for properly locating said enclosure on said cylinder head to be inspected.

21. The device of claim 13, further comprising at least one sensor for indicating proper location of said enclosure to said cylinder head to be inspected.

22. The device of claim 13, wherein either of said motive assemblies includes a motive device selected from the group consisting of an electro-mechanical cylinder, a pneumatic cylinder and a hydraulic cylinder.

23. The device of claim 13, further comprising a protective housing substantially surrounding each fiber-optic probe, said protective housing for shielding its fiber-optic probe from potential damage due to contact with said cylinder head and or blockage material present in an associated coolant passage.

24. The device of claim 13, further comprising an interior and/or exterior wiping element located around each fiber-optic probe aperture in said enclosure, said wiping elements provided to clean debris from an associated fiber-optic probe housing as it is withdrawn into said enclosure.

25. The device of claim 13, wherein said enclosure is pressurized to minimize or prevent the entry of contamination thereto.

26. The device of claim 13, further comprising quick-change electrical and or pneumatic connectors for facilitating disconnection and removal of said enclosure from its motive assembly.

27. The device of claim 13, further comprising a display for indicating the presence of a coolant passage blockage.

28. The device of claim 27, wherein the relative location of said blockage(s) is indicated on said display.

29. The device of claim 13, further comprising a communication link with one or more other cylinder head manufacturing-related devices, such that detection of a coolant passage blockage can cause or prevent further action(s) relating to manufacture and/or use of the affected cylinder head.

30. A method for detecting a blockage within a coolant passage of a vehicle cylinder head, comprising:

providing a fiber-optic probe for emitting and receiving light;

inserting said a fiber-optic probe into a coolant passages to be inspected;

causing said fiber-optic probe to emit light into said coolant passage;

if emitted light is reflected back to and received by said fiber-optic probe, using a sensor in communication with said fiber-optic probe to register said reflected light;

withdrawing said fiber-optic probe from said coolant passage; and comparing any reflected light readings registered by said sensor to a threshold value to determine if any blockages are present within said coolant passage.

31. The method of claim 30, wherein a plurality of fiber-optic probes are present and are used simultaneously to inspect a plurality of coolant passages.

32. The method of claim 30, wherein the number of said fiber-optic probes is equivalent to the number of coolant passages present in said cylinder head.

33. The method of claim 30, wherein insertion and withdrawal of said fiber-optic probe to/from said coolant passage to be inspected is performed by hand.

34. The method of claim 30, wherein insertion and withdrawal of said fiber-optic probe to/from said coolant passage to be inspected is performed by a motive device selected from the group consisting of an electro-mechanical cylinder, a pneumatic cylinder, a hydraulic cylinder, and a robot.

35. The method of claim 30, further comprising providing an enclosure for housing at least said fiber-optic probe, said at least one fiber-optic probe extending through a corresponding aperture in said enclosure when in an inspection position.

36. The method of claim 35, wherein said enclosure is moveable toward and away from a cylinder head to be inspected.

37. The method of claim 36, wherein said enclosure is floatingly suspended by a motive assembly such that said enclosure can self-align with a mating surface of said cylinder head to be inspected upon contact therewith.

38. The method of claim 35, wherein said at least one fiber-optic probe is moveable within said enclosure toward and away from a cylinder head to be inspected.

39. The method of claim 30, wherein said threshold level of reflected light can be adjusted to permit the presence of blockages of insignificant size.

40. The method of claim 30, further comprising a means of alerting an operator to the presence of a blockage(s).

41. The method of claim 30, further comprising a display for indicating the inspection status of a cylinder head.

42. The method of claim 41, wherein the relative location of a detected blockage(s) is indicated.

* * * * *